United States Patent
Nilsson

(10) Patent No.: US 8,241,652 B2
(45) Date of Patent: Aug. 14, 2012

(54) POROUS GELATIN MATERIAL, GELATIN STRUCTURES, METHODS FOR PREPARATION OF THE SAME AND USES THEREOF

(75) Inventor: Kjell Nilsson, Bjuv (SE)

(73) Assignee: Celltrix AB, Astorp (SE)

( * ) Notice: Subject to any disclaimer, the term of this patent is extended or adjusted under 35 U.S.C. 154(b) by 1104 days.

(21) Appl. No.: 12/134,941

(22) Filed: Jun. 6, 2008

(65) Prior Publication Data

US 2008/0260793 A1     Oct. 23, 2008

Related U.S. Application Data

(62) Division of application No. 10/516,614, filed as application No. PCT/SE03/00836 on May 23, 2003, now Pat. No. 7,404,971.

(60) Provisional application No. 60/389,937, filed on Jun. 20, 2002.

(30) Foreign Application Priority Data

Jun. 11, 2002 (SE) .................................. 0201779

(51) Int. Cl.
*A61K 9/00* (2006.01)
*C12N 5/00* (2006.01)
(52) U.S. Cl. .................. 424/422; 424/400; 424/489
(58) Field of Classification Search .................. 424/400, 424/422, 489
See application file for complete search history.

(56) References Cited

U.S. PATENT DOCUMENTS

| | | | |
|---|---|---|---|
| 4,123,382 A | 10/1978 | Morse et al. | |
| 4,935,365 A | 6/1990 | Nilsson et al. | |
| 5,015,576 A | 5/1991 | Nilsson et al. | |
| 5,541,234 A | 7/1996 | Unger et al. | |
| 5,629,191 A | 5/1997 | Cahn | |
| 5,830,493 A * | 11/1998 | Yokota et al. | 424/426 |
| 5,866,155 A | 2/1999 | Laurencin et al. | |
| 5,958,541 A * | 9/1999 | Miller et al. | 428/64.1 |

FOREIGN PATENT DOCUMENTS

| | | |
|---|---|---|
| EP | 0222718 | 5/1987 |
| WO | WO8200660 | 3/1982 |
| WO | WO0017257 | 3/2000 |

* cited by examiner

*Primary Examiner* — Ruth Davis
(74) *Attorney, Agent, or Firm* — Morgan, Lewis & Bockius LLP

(57) ABSTRACT

The present invention relates to a porous gelatin material in the form of spherical particles with a continuous pore structure and cast, three-dimensional, porous gelatin structures. The invention also comprises methods for preparation of the porous gelatin materials and structures. The method for preparing the porous gelatin material in the form of spheres with a continuous pore structure comprises the steps of preparing a homogenous water-based gelatin solution, adding an emulsifier with an HLB value >9, adding a first composition comprising an organic solvent and an emulsifier with an HLB value >9, adding a second composition comprising an organic solvent and an emulsifier with an HLB value <8 and allowing the gelatin material to solidify. Uses of the materials according to the invention are also included.

7 Claims, No Drawings

POROUS GELATIN MATERIAL, GELATIN STRUCTURES, METHODS FOR PREPARATION OF THE SAME AND USES THEREOF

RELATED PATENT INFORMATION

This is divisional of U.S. patent application Ser. No. 10/516,614 filed on Dec. 3, 2004 now U.S. Pat. No. 7,404,971, which is a filing under 35 U.S.C. §371 of International Application No. PCT/SE03/00836, filed May 23, 2003 that designates the United States of America, and the benefit is claimed under 35 U.S.C. §119(a)-(d) of Swedish Application No. 0201779-6, filed Jun. 11, 2002, and under 35 U.S.C. §119(e) of U.S. Provisional Application No. 60/389,937, filed Jun. 20, 2002.

FIELD OF THE INVENTION

The present invention relates to a porous gelatin material with a continuous structure in the form of spherical particles, cast, three-dimensional, porous gelatin structures, methods for producing the same and uses thereof.

BACKGROUND ART

Most animal cells are surface-dependent, that is they have to be attached to a surface to be able to survive and/or proliferate. Traditionally this surface has been the interior of glass or plastic flasks. Great difficulties have been involved in culture of cells on a large scale or in implantation of the cells. The size of these cells is 5-20 μm.

Microcarriers are small particles of 0.2 mm diameter, to which the cells can attach and on which they can proliferate (van Wezel, A. L. Nature 216 (1967) 64-65 Growth of cell strains and primary cells on microcarriers in homogeneous culture). These particles have to some extent made it easier to culture surface-dependent cells on a large scale.

The most common type of microcarrier consists of spherical carriers made of dextran and modified by derivatisation with positive groups. This makes the cells adhere to the carriers. Another way of making the cells adhere is either to produce the carriers of gelatin or to link gelatin to the surface of dextran particles. Gelatin is made of collagen which is the substance to which cells normally adhere. The carriers that are currently available for cells are not optimal in every respect. These carriers are often homogeneous, that is the cells can only adhere/grow on their surface. As a result, the surface available for cell adhesion/cell growth will be limited to the surface area of the carriers. Furthermore, the cells can only adhere/grow in two dimensions in comparison to normally three dimensions in vitro. Another limitation of prior-art systems is that when the carriers are used for culture in culture vessels the cells will be damaged by the forces caused by the stirring system.

To some extent this has already been solved by preparing particles having a great number of encased cavities by means of an emulsion method (Kjell Nilsson and Klaus Mosbach, Swedish Patent 8504764-5, Macroporous particles, method for its production and use of the same). This patent specification discloses how particles having a great number of encased cavities can be prepared by adding to an aqueous solution of the matrix material a solid, liquid or gaseous cavity-forming compound. After the particles have formed by dispersion in a water-insoluble dispersing agent, the matrix is made water-insoluble by cooling, covalent crosslinking or polymerisation. The cavity-forming compound is removed to obtain the encased cavities.

The particles can be used as ion exchangers, gel filter media, chromatography media and microcarriers in cell culture. The matrix is made of protein, polysaccharide or polyacrylamide.

The invention according to Swedish Patent 8504764-5 provided particles in which some of the cavities of the particles were available for cell adhesion/cell growth. It has however been found that the thus-obtained particles were not optimal in some respects. Optimally all the cavities are interconnected so that a continuous porous phase and a continuous matrix phase are obtained. In the present invention, this state was unexpectedly obtained in the case of gelatin by a combination of emulsifier and solvent.

In addition, this state has made it possible to pre-pare both particles and other three-dimensional shapes. This phase separation must be stable on a micro-level for the length of time necessary for the preparation of the desirable shapes. Furthermore the phase separation must not result in a separation of the phases on a macro-level since this yields shapes without porosity.

SUMMARY OF THE INVENTION

According to one aspect, the present invention relates to a method for preparation of a porous gelatin material, in the form of spheres, with a continuous pore structure, the method comprising the steps of: preparing a homogeneous water-based gelatin solution; adding an emulsifier with an HLB value >9; adding a first composition comprising an organic solvent and an emulsifier with an HLB value >9; adding a second composition comprising an organic solvent and an emulsifier with an HLB value <8; and allowing the gelatin material to solidify.

According to a second aspect, the invention relates to a porous gelatin material, in the form of spherical particles, with a continuous pore structure produced by preparing a homogeneous water-based gelatin solution; adding an emulsifier with an HLB value >9; adding a first composition comprising an organic solvent and an emulsifier with an HLB value >9; adding a second composition comprising an organic solvent and an emulsifier with an HLB value <8; and allowing the gelatin material to solidify.

According to a further aspect, the invention relates to a method for producing a cast, three-dimensional, porous gelatin structure which can be obtained by preparing a homogenous water-based gelatin solution; adding an emulsifier with an HLB value >9; adding a first composition comprising an organic solvent and an emulsifier with an HLB value >9; and casting the gelatin solution in a mould.

According to another aspect, the invention relates to a cast, three-dimensional, porous gelatin structure which can be obtained by preparing a homogenous water-based gelatin solution; adding an emulsifier with an HLD value >9; adding a first composition comprising an organic solvent and an emulsifier with an HLD value >9; and casting the gelatin solution in a mould.

According to yet another aspect, the invention relates to use of a porous gelatin material or a cast, three-dimensional, porous gelatin structure produced according to the present invention, as carrier for cells.

According to a further aspect, the invention relates to use of a porous gelatin material or a cast, three-dimensional, porous gelatin structure produced as described above for making an implant.

Another aspect of the present invention involves a method for implanting a biocompatible, porous gelatin is material as described above or a cast, three-dimensional, porous gelatin structure as described above as carrier for cells in an individual for production of substances, comprising implanting in said biocompatible, porous gelatin material or said cast, three-dimensional, porous gelatin structure in the individual and subsequently allowing the cells on the biocompatible, porous material or the cast, three-dimensional, porous gelatin structure to produce said substances.

DETAILED DESCRIPTION OF THE INVENTION

According to one embodiment of the invention, the above methods further comprise the step of chemically crosslinking the gelatin material. This crosslinking can be carried out with poly- or bifunctional isocyanate compounds, such as hexamethylenediisocyanate or toluene-diisocyanate, poly- or bifunctional aldehydes, such as glutardialdehyde. Gelatin can also be crosslinked with formaldehyde in liquid form or in gaseous form.

According to another embodiment, the emulsifier is selected with an HLB value >9 from, but not exclusively, the group consisting of Tween 80 (polyoxysorbitan monooleate, HLB value=15), Tween 40 (polyoxyethylene stearic acid, HLB value=15), Myrj 52 (polyoxyethylene stearic acid, HLB value=17) and Brij 58 (polyoxyethylene cetyl alcohol HLB value=16).

According to yet another embodiment, the emulsifier is selected with an HLB value <8 from, but not exclusively, the group consisting of Span 85 (HLB value=2), Span 65 (HLB value=2) and Atmos 300 (HLB value=2.5).

"Atmos" is the trademark of a series of mono- and diglyceride emulsifiers which are used in ice cream and frozen desserts (The Condensed Chemical Dictionary, 6th Edition, 1961, p. 116).

According to another embodiment, the organic solvent is selected from, but not exclusively, the group consisting of cyclohexane, toluene, paraffin oil and industrial oil.

According to a particularly preferred embodiment according to the invention, the organic solvent is cyclohexane.

The selection of emulsifier in the present methods according to the invention is not critical as long as the requirement on the HLB value of the emulsifier is fulfilled. It will be obvious to the one skilled in the art which emulsifiers can be selected as arbitrary agents.

Emulsifiers are characterized by the hydrophilic-lipophilic balance being stated in the form of HLB values. They usually vary between 1 and 20. A low HLB value indicates that the lipophilic part of the emulsifier dominates and a high value that the emulsifier has primarily hydrophilic properties (Galenisk farmaci, Erik Sandell, $3^{rd}$ Edition, 1982, p. 97).

In 8504764-5, the pore structure is produced by emulsifying, in one of the steps of the preparation, an organic solvent in the homogeneous gelatin solution. This emulsion is stabilized with an emulsifier, for instance Span 85, with an HLB value <8. This type of emulsifier yields stable emulsions of solvent in water phases. After cooling below the solidification point of the gelatin solution, the solvent is removed. The result is a material having a great number of encased cavities which are not interconnected.

According to the present invention, a continuous pore structure is prepared by adding to a homogeneous water-based gelatin solution, in one of the steps of the preparation process, a solvent, for instance cyclohexane, containing an emulsifier with an HLB value >9. This type of emulsifier yields stable emulsions of water phases in solvents. However, since the volume of the water phase is much greater than the volume of the solvent phase, this results in an unstable proportion. This unstable proportion results in an unexpected microscopic phase separation which is stable for a length of time which is sufficient to prepare the desirable shapes. The addition of an emulsifier with an HLB value >9 to the gelatin phase facilitates the microscopic phase separation. Another feature distinguishing the present invention from prior-art technique is that the present invention only works when gelatin is used as matrix-forming compound. Experiments carried out with polysaccharides and polyacrylamide do not result in any microscopic phase separation. Thus using present-day knowledge, the new invention only works with gelatin as matrix-forming compound. Therefore something unique and unexpected happens in the combination of gelatin and the emulsifier system. As mentioned above, the invention disclosed in 8504764-5 provides encased cavities in a great number of matrix-forming materials and since the cavities of the particles are not interconnected, the maximum number of cells cannot adhere/grow. In 8504764-5 discrete droplets/pores are thus obtained, but according to the present invention two continuous phases are obtained, one gelatin-water phase and one solvent phase, which in the solidification provide a continuous pore structure.

The addition of the first composition to the gelatin solution results in a phase separation at a given temperature. The different phases are not visible with the naked eye but the mixture becomes whitish. According to one embodiment of the present invention, three-dimensional gelatin structures can be obtained by casting the gelatin solution, after adding the first composition to the gelatin solution, in a mould. The mould can be any type of mould and adjusted to the intended final use of the gelatin structure. For instance, the gelatin structure is cast to tubes, ears or other in-vivo-like structures, such as fingers, toes, nipples or noses.

The addition of the second composition (cyclohexane containing Span 85) to the gelatin solution yields droplets surrounded by solvent, said droplets being stabilised by Span 85. These droplets contain a gelatin phase and a solvent phase. Both phases are continuous. The addition of the second composition results in spherical particles.

According to another embodiment of the invention, the biocompatible, porous material or the cast, three-dimensional gelatin structure is used to culture artificial skin, artificial organs, fatty tissue and blood vessels.

The biocompatible, porous material according to the present invention can be used both as carrier for cells in cell culture and as carrier for existing cells for the production of a desirable substance before/after implantation in an individual. The cells can be either the individual's own cells or cells from another source (characteristic of the species or foreign to the species). In some cases the cells as such can be the desirable product, for instance attached initial stages of adipocytes (preadipocytes) on the carrier which after implantation can proliferate so as then to be converted into adipocytes (fat cells). One field of application is for instance plastic surgery.

It is also possible to implant the produced porous structures according to the invention in a human body without the addition of cells. After implantation, the neighbouring cells in the body will migrate into and colonise the structure. After the implanted structure has dissolved, the colonised cells will have formed a structure corresponding to the implant. The crosslinking degree of the gelatin material controls the time it takes for the gelatin structure to dissolve in the body. It is thus possible to control the dissolution for the intended application. An example of this is in plastic surgery where carriers according to the invention without accompanying cells are injected at the seat of a wrinkle. The cells surrounding the carriers migrate towards the carriers and colonise them. Gradually, as the carriers are being dissolved by surrounding enzymes the migrated cells occupy the seat of the wrinkle. This results in the wrinkle being smoothed out.

Yet another example is to use the material with adhering cells when testing drugs. By measuring variables which reflect the state of the adhering cells, predictions can be made about the effectiveness/toxicity of the potential drug.

Another example is skin cells on the carrier which can be used for treating different types of injuries to the skin. Another example is myoblasts (muscle cells) which can be used in treatment of e.g. cardiac infarction. One more example is hepatocytes (liver cells) which can be used to render toxic substances in liver lesions harmless. Also more complex structures such as islets of Langerhans can be attached to and/or in the porous carrier. Islets of Langerhans are composed of a plurality of different cell types and constitute the system that regulates the blood sugar level. These islets are considerably larger and require a pore size of the carrier of 50-200 μm.

The term "substance" used herein relates to the substances that can be produced by different cells or microorganisms, for instance antibiotics, pharmaceutical substances, e.g. dopamine which is a key substance in. Parkinson's disease, and different interferons which are active substances in treatment of cancer.

The term "porous" used herein in combination with both the spherical particles and the cast three-dimensional gelatin structures relates to the fact that the particles and the structures comprise pores in which cells can grow.

According to the invention, the degradability of the biocompatible, porous gelatin material is determined by the degree of crosslinking of the gelatin. An agent can, for instance, be added to enhance or change the adhesion of cells to said biocompatible, porous material during casting of the dispersion, or the agent can be bound chemically to the polymer or added later. Agents affecting cell adhesion can be either simple molecules or proteins. Examples of the former are positively or negatively charged substances, such as hexamethylene diamine and amino capronic acid. Also uncharged structures such as fatty acids can be attached to the matrix. Examples of more complex structures are peptides containing the amino acid sequence arginine-glycine-aspargine or derivatives thereof. This sequence promotes the adhesion of cells to the carrier. Examples of proteins are fibronectin and laminin. Also non-defined mixtures of proteins (obtained by extraction of tissues), such as ECM (extracellular matrix), can be used.

To prevent rejection, the gel particles can be encapsulated with adhering cells in another material which serves to prevent cells and proteins of the body from recognizing or reacting with the adhering cells. This material can be a polysaccharide or polymer. The material thus functions as a kind of mechanical barrier against the proteins and cells of the body.

There are several types of gelatin depending on the preparation method and raw material used in the production. These gelatin types have different properties which can be used to provide the porous material with various properties. Furthermore, the gelatin can be modified before preparation to obtain further new and desirable properties. This modification can be carried out by means of physical methods, such as fractionation, or chemical reactions.

To obtain a shape suitable for the specific application, the prepared dispersion can be formed into different three-dimensional structures according to prior-art methods. Thus spherical particles can be prepared by an emulsion process and membranes by casting on/between plates. Special structures can be cast in specially made moulds, for instance ears. Finishing processes involving mechanical methods can also be used to obtain the final structure.

The biocompatible, porous material is prepared so that the cells are present both inside the continuous pore structure and outside the biocompatible, porous material. This results in optimal use of the material.

In the present description the expression "carrier for cells" is intended to comprise carriers which can be used in culture of different cells and carriers which can be used for cells to achieve production of desirable substances. The expression "carrier for cells" also includes medical implants for implantation in the human body. A surprising effect in the preparation of the biocompatible, porous gelatin material according to the invention is that the continuous pores obtained in the material are uniformly distributed through the cross-section of the material. Thus, a more uniform distribution of the cells in the biocompatible, porous gelatin material is achieved.

EXAMPLES

Example 1

Preparation of Spherical Gelatin Particles With Large Continuous Pores

While stirring 13 g gelatin is dissolved in 100 ml water by heating to 40° C. All subsequent steps are carried out while stirring. To this solution 21 g Tween 80 (polyoxyethylene(20) sorbitanmonooleate) is added. Tween is the trademark of a series of emulsifiers and surfactants. They are polyoxyethylene derivatives of fatty acid partial esters of hexitolanhydrides (The Condensed Chemical Dictionary, $6^{th}$ Edition, 1961, p. 1182). The mixture is cooled to 35° C. Then 34 ml cyclohexane containing 1 g Tween 80 is added. The mixture is further cooled to 32° C., whereupon 34 ml cyclohexane containing 2 g Span 85 (sorbitantrioleate) is added. Span is the trademark of a series of emulsifiers and surfactants. They are fatty acid partial esters of hexitolanhydrides (or sorbitan) (The Condensed Chemical Dictionary, $6^{th}$ Edition, 1961, p. 1063). The mixture is further cooled until the gelatin solidifies. Emulsifiers and cyclohexane are removed by washing with acetone. The particles can be dried by allowing the acetone to evaporate.

Example 2

Preparation of Spherical Gelatin Particles With Small Continuous Pores

While stirring 13 g gelatin is dissolved in 100 ml water by heating to 40° C. All the subsequent steps are carried out while stirring. To this solution 15 g Tween 80 is added. The mixture is cooled to 35° C. Then 12 ml cyclohexane containing 1.5 g Tween 80 is added. The mixture is further cooled to 32° C., whereupon 58 ml cyclohexane containing 3 g Span 85 is added. The mixture is further cooled until the gelatin solidifies. Emulsifiers and cyclohexane are removed by washing with acetone. The particles can be dried by allowing the acetone to evaporate.

Example 3

Crosslinking Method 1

10 g porous material is mixed with 120 ml acetone and 30 ml water in which 480 mg sodium acetate trihydrate is dissolved. The material is crosslinked for two hours by the addition of 0.45 ml hexamethylenediisocyanate and 0.06 ml triethylamine. The crosslinked particles are washed with water and acetone. The particles are dried by allowing the acetone to evaporate.

Example 4

Crosslinking Method 2

10 g porous material is mixed with 400 ml water in which 7.2 g sodium phosphate is dissolved. The material is crosslinked for one hour by the addition of 0.8 ml hexamethylenediisocyanate and 5 µl triethylamine. The crosslinked particles are washed with water and acetone. The particles are dried by allowing the acetone to evaporate.

In the production of the material above, larger continuous pores can be obtained by using a higher Tween concentration. By increasing the amount of cyclohexane, larger pores are also obtained and simultaneously a larger total pore volume is obtained. By increasing the stirring rate, smaller pores are obtained. It is thus easy to vary the porosity of the membrane within wide limits.

The resistance of the biocompatible, porous material to heat, enzymes, etc. is proportional to the crosslinking degree. An increased concentration of crosslinking agent, for instance hexamethylene diisocyanate, results in increased resistance. An increased crosslinking time also results in increased resistance. The crosslinking reagents that are used in the preparation can be, for instance, bifunctional or polyfunctional, such as diisocyanates and polyisocyanates, but also aldehydes can be bi- and polyfunctional. Other prior-art methods of cross-linking gelatin can be used.

The crosslinking can take place in the preparation of the particles by adding the crosslinking reagent to the dispersion before forming. As an alternative, the structures formed can be crosslinked on a subsequent occasion since the porous gelatin structure is maintained as the gelatin solidifies when cooling.

The invention claimed is:

1. A porous gelatin material for implantation into a human body in the form of a plurality of porous spheres with a continuous pore structure throughout each sphere, with the pores extending to the surface of each sphere, whereby the spheres are formed by a method that includes the steps of:
preparing a homogeneous water-based gelatin solution;
adding an emulsifier with an HLB value >9;
adding-a-first composition comprising an organic solvent and an emulsifier with an HLB value >9;
adding a second composition comprising an organic solvent and an emulsifier with an HLB value <8; and
allowing the gelatin material to solidify.

2. A porous gelatin material in the form of porous spheres with a continuous pore structure as claimed in claim 1, wherein the gelatin has been chemically crosslinked.

3. A cast, three-dimensional, structure formed of porous gelatin for implantation into the human body with a continuous pore structure throughout the structure, wherein the pores extend to the outer surface of the structure so the pores are exposed to cells that will grow in the pores after implantation in a human body, the structure being formed by a method that comprises the steps of:
preparing a homogenous water-based gelatin solution;
adding an emulsifier with an HLB value >9;
adding a first composition comprising an organic solvent and an emulsifier with an HLB value >9; and
casting the gelatin solution in a mould.

4. A cast, three-dimensional, porous gelatin structure with a continuous pore structure as claimed in claim 3, wherein the cast three-dimensional gelatin structure is selected among tubes, ears and structures suitable for in-vivo implantation in the human body.

5. A cast, three-dimensional, porous gelatin structure with a continuous pore structure as claimed in claim 3, wherein the gelatin has been chemically crosslinked.

6. A culture of artificial skin, artificial organs, or fatty tissue and blood vessels comprising a biocompatible porous material in the form of a plurality of porous spheres with a continuous pore structure throughout each sphere with the pores extending to the outer surface of each sphere, or a cast, three-dimensional, porous gelatin structure with a continuous pore structure throughout the subject, wherein the pores extend to the outer surface of the subject, the material and object being formed by a method that comprises the steps of:
preparing a homogeneous water-based gelatin solution;
adding an emulsifier with an HLB value >9;
adding-a-first composition comprising an organic solvent and an emulsifier with an HLB value >9;
adding a second composition comprising an organic solvent and an emulsifier with an HLB value <8; and
allowing the gelatin material to solidify.

7. The culture of artificial skin, artificial organs, or fatty tissue and blood vessels as claimed in claim 6, wherein the cast, three-dimensional, porous gelatin structure with a continuous pore structure is selected among tubes, ears, and structures suitable for in-vivo implantation in the human body.

* * * * *